United States Patent [19]

Hendren, III

[11] 3,986,493

[45] Oct. 19, 1976

[54] ELECTROMAGNETIC BOUGIENAGE METHOD

[76] Inventor: William Hardy Hendren, III, 76 Crafts Road, Brookline, Mass. 02146

[22] Filed: July 28, 1975

[21] Appl. No.: 599,842

[52] U.S. Cl. .................................. 128/1.3; 128/335
[51] Int. Cl.² ................... A61B 17/52; A61B 17/08
[58] Field of Search .................. 128/24 R, 1.3, 1.4, 128/1.5, 75, 303 R, 84 R, 335, 334 R, 334 C, 51, 52

[56] References Cited
UNITED STATES PATENTS

| | | | |
|---|---|---|---|
| 2,863,458 | 12/1958 | Modny et al. | 128/303 |
| 2,897,411 | 7/1959 | Brown et al. | 128/1.4 UX |
| 3,674,014 | 7/1972 | Tillander | 128/1.3 |
| 3,771,526 | 11/1973 | Rudie | 128/334 C |

Primary Examiner—Lawrence W. Trapp
Attorney, Agent, or Firm—Thompson, Birch, Gauthier & Samuels

[57] ABSTRACT

A method for lengthening atretic segments of a patient by electromagnetic bougienage to facilitate subsequent primary anastomosis without tension. In the preferred method, two magnetic bougies are inserted into the atretic segments so that the magnetic bougies are positioned at the closed ends of the segments. An annular electromagnet is placed around the patient's body and is cycled on and off to urge the magnetic bougies towards each other over a period of time in order to lengthen the atretic segments. The magnetic bougies are then withdrawn after which primary anastomosis is accomplished.

17 Claims, 8 Drawing Figures

U.S. Patent   Oct. 19, 1976   Sheet 1 of 2   3,986,493
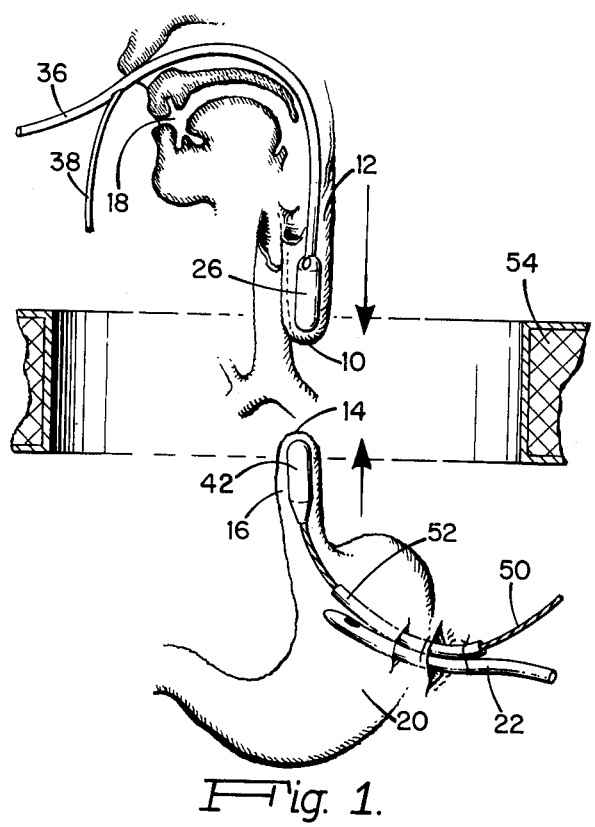
Fig. 1.
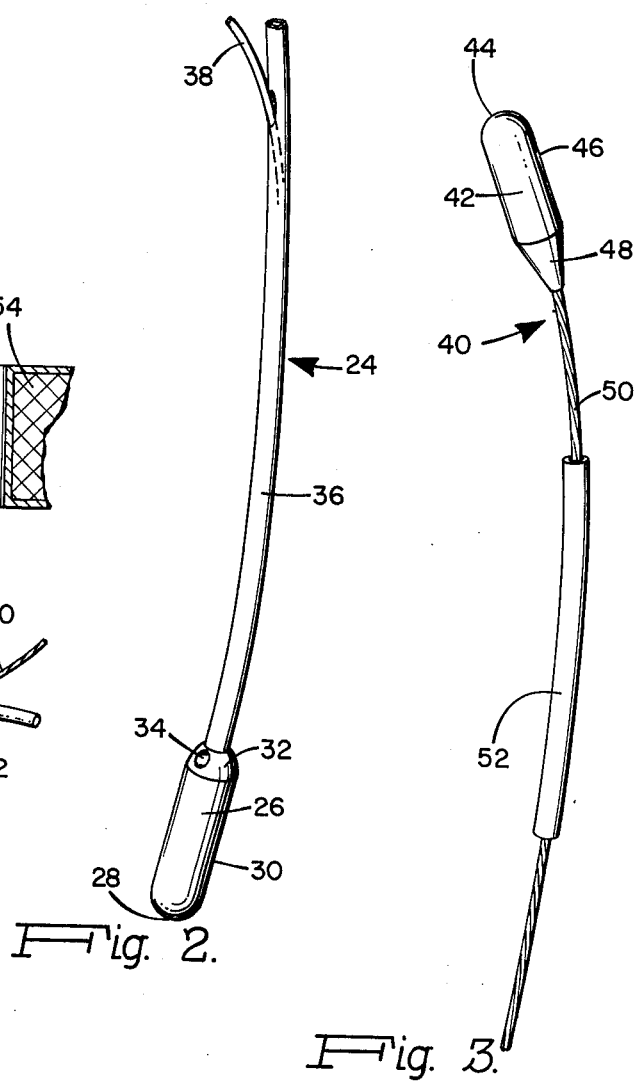
Fig. 2.
Fig. 3.
Fig. 4.
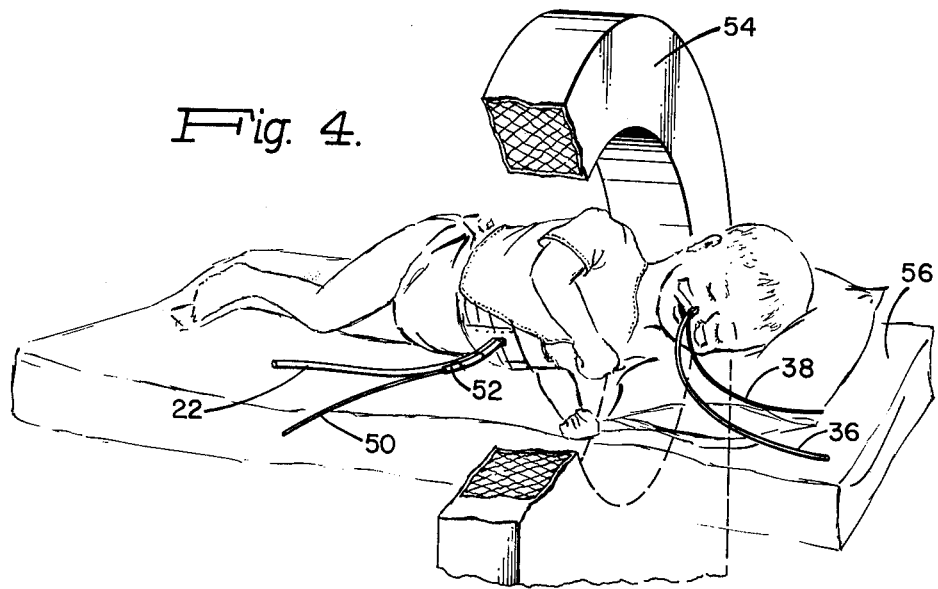

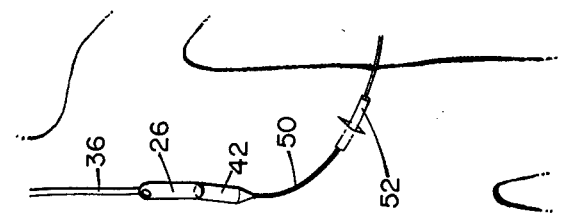
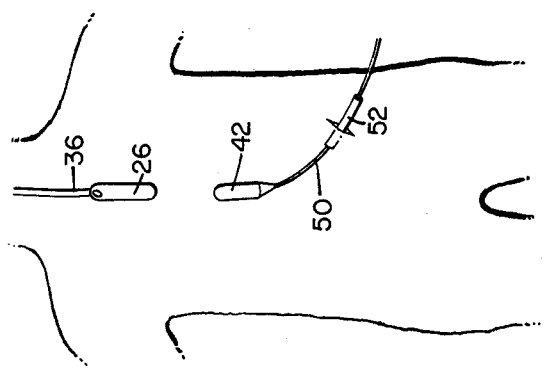
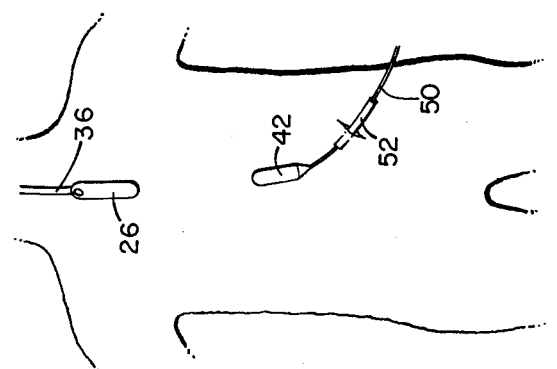
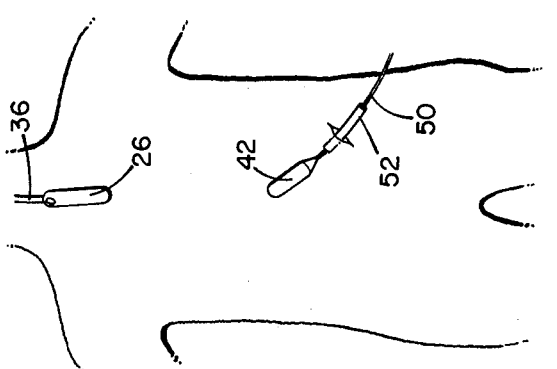

ELECTROMAGNETIC BOUGIENAGE METHOD

BACKGROUND OF THE INVENTION

Some cases of congenital esophageal atresia are not suitable for immediate treatment by primary anastomosis because the closed ends of the atretic segments are spaced too far apart to be joined without undue tension. The most widely used previous method to treat this type of condition has been to interpose a segment of colon between the atretic esophageal segments at a later age. This method is described by Azar et al, *J. Pediatric Surgery* 6:3-9(1971).

However, the nerves in the colonic segment function somewhat differently from the nerves in the esophageal segments and, therefore, the rhythmic contracting (tensing) and dilating (relaxing) of the joined different segments is relatively nonuniform and inefficient for transporting food from the mouth to the stomach. For this reason, the method of this invention is believed to be a considerable improvement over the colon interposition method because the repaired esophagus of this invention contains only esophageal tissue.

SUMMARY OF THE INVENTION

The preferred method of this invention prepares a patient with esophageal, rectal or other atresia for subsequent primary anastomosis without tension. This method uses two bougie assemblies, each having a leading magnetic bougie and trailing retrieval means. The bougie assemblies are inserted into the atretic segments so that the magnetic bougies are positioned at the closed ends of the atretic segments and the retrieval means extend externally of the patient. Then, the patient is placed within the circular opening of an electromagnet so that the two bougies are aligned with the axis of the electromagnet and are spaced-apart on either side of and approximately equidistant from the plane of the core of the electromagnet.

The electromagnet is cycled so that it is energized for approximately 60 seconds and is de-energized for approximately 90 seconds for a period of a number of days. This causes the two bougies to be magnetically urged towards each other until the closed segment ends are virtually touching. Then, the bougie assemblies are removed by withdrawing the retrieval means and primary anastomosis can subsequently be performed.

An alternative method of this invention does not use an external electromagnet. Instead, the magnetic bougies are themselves electromagnets which can be cyclically energized in the same manner as the previously described external electromagnet.

DESCRIPTION OF THE DRAWINGS

FIG. 1 is a schematic diagram of a patient whose upper esophageal pouch is not connected to his lower esophageal pouch because of esophageal atresia. The two bougie assemblies and the electromagnet are also shown.

FIG. 2 is a perspective view of the first or upper bougie assembly which incorporates a suction tube.

FIG. 3 is a perspective view of the second or lower bougie assembly which includes a hollow cable sheath which is usually attached to a gastrostomy tube.

FIG. 4 is a perspective view of an infant patient positioned horizontally within the core of an electromagnet. The first bougie assembly extends through the patient's nose. The gastrostomy tube and the second bougie assembly extend through the patient's abdominal wall.

FIGS. 5–8 are schematic time sequence views of the patient's body showing the progressive drawing together of the magnetic bougies during the duration of the treatment.

DESCRIPTION OF THE PREFERRED AND ALTERNATE METHODS OF TREATMENT

FIG. 1 shows a cut-away schematic diagram of an infant patient who has esophageal atresia. It will be seen that the closed end 10 of the upper esophageal atretic segment 12 is spaced too far from the closed end 14 of the lower esophageal atretic segment 16 to allow safe primary anastomosis without tension. This situation occurs in approximately 10% to 20% of all cases of esophageal atresia.

An infant who has esophageal atresia cannot be fed by mouth because the food cannot pass through the interrupted esophagus from the mouth 18 to the stomach 20. Therefore, FIG. 1 shows a conventional gastrostomy tube 22 extending through a small upper abdominal incision into the stomach 20. The patient is fed through tube 22.

After it has been decided to repair the atretic condition by use of the method of this invention, treatment can be started as soon as the infant's size and general condition have reached an acceptable level. If use of the inventive technique is anticipated, the gastrostomy site should be located near the patient's midline so that the gastrostomy tube 22 will have a generally straight and upward orientation in the mediastinum. FIG. 1 shows the more conventional and less preferred gastrostomy site to the left of the midline.

The apparatus used in the inventive method will now be described. This will be followed by a description of the preferred method. Finally, a description of the alternate method and apparatus will be given.

This invention utilizes two magnetic bougies and a means for magnetically urging the two bougies together. In this specification, the word "magnetic" means capable of being magnetized. FIG. 2 shows the upper bougie assembly 24 which is adapted to be inserted into the upper atretic segment 12. Assembly 24 includes a magnetic bougie 26 made of ferrous material, such as steel, which has a rounded leading end or nose 28, a solid cylindrical body 30, and a hollow streamlined trailing end 32. For suction purposes, to be described later, a number of fluid openings 34 are provided in the trailing end 32 of upper bougie 26.

Bougie 26 is attached at its hollow trailing end 32 to a hollow suction tube 36 which is connected at its other end to unshown sump suction producing means. A small vent tube 38 is passed through a side opening in suction tube 36 to act as an air vent and to facilitate occasional saline solution flushing of the upper esophageal pouch. The accumulation of saliva in the upper esophageal segment 12 is prevented by the aspiration of the saliva through fluid openings 34, through suction tube 36, and into the unshown suction producing means.

FIG. 3 shows the lower bougie assembly 40 which is adapted to be inserted into the lower atretic segment 16. Assembly 40 includes a magnetic bougie 42, similar in virtually all respects to magnetic bougie 26, having a rounded leading end 44, a solid cylindrical body 46, and a hollow streamlined trailing end 48. Bougie 42 is attached at its trailing end 48 to a stranded stainless steel semi-flexible retrieval cable 50 which is slidably retained in a tubular cable sheath 52.

FIGS. 1 and 4 show a representation of the annular electromagnet 54 used in the preferred method of this invention. Preferably, it is a water-cooled, air solenoid electromagnet which is energized by a high amperage, low voltage source of direct current power. The power is cycled on and off by an unshown automatic sequencing control unit. The magnet 54 must have a core of sufficient diameter to permit the infant patient to lie on a special mattress 56 which extends through the core as shown in FIG. 4.

The preferred method of treatment using the aforementioned equipment will now be described. Preliminarily, under general anesthesia, a gastrostomy is performed on the infant patient (who is usually less than 1 day old). During the subsequent period of several days or weeks, the infant is fed via gastrostomy and maintained on sump suction to the upper esophageal pouch. When the infant's condition is satisfactory, he is again placed under general anesthesia. The upper bougie assembly 24 is placed into the upper esophageal segment 12 so that the upper bougie 26 is positioned against the closed end 10 of the upper segment. This placement is accomplished by use of a McGill forceps through the mouth 18. The suction tube 36 is brought out through a nostril and the vent tube 38 is passed through the side opening in the suction tube 36.

The lower bougie assembly 40 is placed into the lower esophageal segment 16 so that the lower bougie 42 is positioned against the closed end 14 of the lower segment. This placement is accomplished under direct vision using a number 10 Fr. panendoscope passed through the gastrostomy opening. The stomach is filled with air through the side opening of the panendoscope, instead of liquid. The cable sheath 52 is tied and anchored to the adjacent gastrostomy tube 22 and the lower bougie 42 is pushed against closed end 14 of lower segment 16 by pushing cable 50 along cable sheath 52.

The infant is then placed in his specially constructed bed as shown in FIG. 4 and is positioned so that the imaginary vertical plane of the circular magnet passes between the two closed ends 10 and 14 of the esophageal segments (and therefore between the two bougies 26 and 42). Preferably, the bougies 26 and 42 are positioned along the axis of the magnet core and are equidistant from the vertical plane of the magnet. The suction apparatus is then connected to suction tube 36 (which is taped to the infant's face above the upper lip) and the suction is begun in order to aspirate the saliva.

The power to the magnet is controlled by an automatic sequencing unit so that the electromagnet is normally energized for 60 seconds and then de-energized for 90 seconds. Preferably, the flux rate gradually increases and then decreases. This cycle is repeated continuously except when the infant must be infrequently removed from the magnet for routine care procedures. During those periods, the magnet is de-energized.

The electromagnet produces a force of approximately 5 oz. on a single steel bougie having a diameter of approximately 8 mm. and a length of approximately 20 mm. Obviously, the magnetic force and bougie size are variables and are selected depending upon the desired results.

The electromagnet pulls the two bougies towards each other (see arrows in FIG. 1) which causes the two esophageal segments to elongate. Constant magnetic force would erode the esophageal ends because of pressure necrosis. Therefore, intermittent magnetic force is mandatory.

The spatial gradient of the field produced by the electromagnet creates substantially all of the pull on the bougies until their separation becomes less than about 10 mm. At that point, the bougies also experience mutual attraction because they become highly magnetized. The bougies are made of hysteresis-free material. Therefore, when the electromagnet is de-energized, there is no mutual attraction between the bougies.

FIGS. 5–8 show X-ray representations of the elongation of the upper and lower esophageal segments over a period of time. For example, FIG. 5 shows the first day of typical electromagnetic treatment. FIG. 6 shows the 10th day. FIG. 7 shows the 20th day. FIG. 8 shows the 30th day. The FIG. 8 X-ray indicates that the two segments have sufficiently lengthened so as to permit surgical joinder.

The time period of electromagnetic treatment depends upon many variables. However, when the FIG. 8 situation is achieved, the patient can be removed from the magnet, the two bougie assemblies can be removed, and the two esophageal segments can be surgically joined without tension.

It will be appreciated that although the preferred method of this invention has been described with reference to esophageal atresia, it is known to also apply to rectal atresia. In rectal atresia cases, it is necessary to first perform a diverting colostomy. A magnetic bougie is then inserted into the atretic high pouch and an electromagnet is employed to lengthen it to the perineum. This permits simple perineal anplasty and division of rectourethral fistula instead of requiring abdominal perineal pullthrough which is the current practice for such cases.

Furthermore, the preferred method of this invention should be useful for many other cases of atresia. Also, it should be useful for a wide variety of other medical needs, such as in orthopedic exercising. These are merely examples of the anticipated wide use of this invention.

The alternate method of this invention is to eliminate the air core electromagnet 54 and to use bougies 26 and 42 which are themselves electromagnets. Alternatively, one of the bougies could be an electromagnet and the other bougie could be the same as the bougies of the preferred embodiment. It is recognized that this alternate method and apparatus involves inserting electrical wires into the infant's body and, for that reason alone, may not be practical because of the danger of electrical shock. However, in theory at least, this alternate method and apparatus is feasible.

The steps of the alternate method are similar to those of the preferred method except that the infant is not confined to the core of an external electromagnet. This is a clear advantage over the preferred method.

The above description obviously suggests many possible variations and modifications of this invention which would not depart from its spirit and scope. It should be understood, therefore, that the invention is not limited in its application to the details of method or structure specifically described or illustrated and that within the scope of the appended claims, it may be practiced otherwise than as specifically described or illustrated.

I claim:
1. A method for lengthening atretic segments of a patient by electromagnetic bougienage to facilitate subsequent primary anastomosis without tension, said method comprising the following steps:
   a. inserting a first magnetic bougie into a first atretic segment so that the leading end of the first magnetic bougie is positioned at the closed end of the first segment;
   b. inserting a second magnetic bougie into a second atretic segment so that the leading end of the second magnetic bougie is positioned at the closed end of the second segment;
   c. intermittently electromagnetically energizing the first and second magnetic bougies to urge the two bougies towards each other, said intermittent energizing taking place over a total time period exceeding at least two days; and
   d. after the intermittently magnetized bougies have sufficiently lengthened the atretic segments to permit primary anastomosis without tension, withdrawing the magnetic bougies from the segments.

2. The method of claim 1 wherein the atretic segments are esophageal segments.

3. The method of claim 2 wherein the first magnetic bougie is inserted through the patient's mouth and is passed downwardly into the upper esophageal pouch, and the second magnetic bougie is inserted through the patient's abdominal wall and through the wall of the lower esophageal pouch.

4. The method of claim 3 wherein the first bougie is attached to the leading end of a suction tube, the suction tube is inserted through the patient's mouth and into his upper esophageal pouch, and saliva and other fluids are pumped out of the pouch through the suction tube.

5. The method of claim 1 wherein the atretic segments are rectal segments.

6. The method of claim 3 wherein the second bougie has a semi-flexible retrieval cable attached to its trailing end, the retrieval cable is slidably retained within a hollow cable sheath, and the cable sheath is fixed to a previously implanted gastrostomy tube.

7. The method of claim 6 wherein the second bougie is positioned at the closed end of the second atretic segment by pushing the retrieval cable inwardly within the fixed hollow cable sheath through the abdominal wall and through the wall of the lower esophageal pouch.

8. The method of claim 1 wherein at least one of the magnetic bougies is an electromagnet.

9. The method of claim 1 wherein both of the magnetic bougies are electromagnets.

10. The method of claim 1 wherein an annular electromagnet is placed around the patient's body so that the two magnetic bougies are substantially coincidental with the axis of the core of the electromagnet.

11. The method of claim 10 wherein the two magnetic bougies are positioned on opposite sides of and approximately equidistant from the plane of the core of the electromagnet.

12. The method of claim 10 wherein the magnetic bougies are cyclically energized for approximately sixty seconds and de-energized for approximately ninety seconds.

13. The method of claim 10 wherein the magnetic bougies are made of ferrous metal and have a rounded leading end.

14. The method of claim 13 wherein the ferrous metal magnetic bougies are made of hysteresis-free material which does not mutually attract when de-energized.

15. The method of claim 6 wherein the gastrostomy tube is implanted on the midline of the lower esophageal pouch to permit a substantially vertical positioning of the attached cable sheath.

16. A method for lengthening atretic esophageal segments of a patient by electromagnetic bougienage to facilitate subsequent primary anastomosis without tension, said method comprising the following steps:
   a. inserting a suction tube having a first magnetic bougie at its leading end through the patient's mouth and into the upper esophageal pouch so that the rounded leading end of the first bougie is positioned at the closed end of the first atretic segment;
   b. applying intermittent sump suction to the suction tube to pump fluids out of the upper pouch;
   c. affixing a hollow open-ended cable sheath to a previously implanted gastrostomy tube and pushing a semi-flexible retrieval cable having a second magnetic bougie at its leading end through the sheath, through the patient's abdominal wall, and through the wall of the lower esophageal pouch so that the rounded leading end of the second bougie is positioned at the closed end of the second atretic segment;
   d. positioning an annular electromagnet around the patient's body so that the two magnetic bougies are positioned substantially along the axis of the core of the electromagnet and on opposite sides of and approximately equidistant from the plane of the core of the electromagnet;
   e. intermittently energizing the electromagnet to urge the first and second bougies towards each other, said intermittent energizing step taking place over a total time period exceeding at least two days; and
   f. after the intermittently magnetized bougies have sufficiently lengthened the atretic segments to permit primary anastomosis without tension, withdrawing the magnetic bougies from the segments.

17. A method for lengthening an atretic segment of a patient by electromagnetic bougienage to facilitate subsequent primary anastomosis without tension, said method comprising the following steps:
   a. inserting a magnetic bougie into an atretic segment so that the leading end of the magnetic bougie is positioned at the closed end of the segment;
   b. intermittently electromagnetically energizing the magnetic bougie to urge the bougie in the direction of the closed end of the segment, said intermittent energizing taking place over a total time period exceeding at least two days; and
   c. after the intermittently magnetized bougie has sufficiently lengthened the atretic segment to permit primary anastomosis without tension, withdrawing the magnetic bougie from the segment.

* * * * *